(12) United States Patent
Lee

(10) Patent No.: US 11,020,047 B2
(45) Date of Patent: Jun. 1, 2021

(54) COMPUTERIZED SENSOR SYSTEM AND MOUTHGUARD DEVICE

(71) Applicant: Otis Dental, LLC, San Francisco, CA (US)

(72) Inventor: Andrew Lee, San Francisco, CA (US)

( * ) Notice: Subject to any disclaimer, the term of this patent is extended or adjusted under 35 U.S.C. 154(b) by 294 days.

(21) Appl. No.: 15/996,335

(22) Filed: Jun. 1, 2018

(65) Prior Publication Data

US 2019/0365311 A1  Dec. 5, 2019

(51) Int. Cl.
| | | |
|---|---|---|
| *A61B 5/00* | (2006.01) | |
| *A61F 5/56* | (2006.01) | |
| *G01L 1/14* | (2006.01) | |
| *H04W 4/80* | (2018.01) | |
| *A61B 90/00* | (2016.01) | |

(52) U.S. Cl.
CPC ............ *A61B 5/4557* (2013.01); *A61B 5/002* (2013.01); *A61B 5/682* (2013.01); *A61F 5/566* (2013.01); *G01L 1/146* (2013.01); *H04W 4/80* (2018.02); *A61B 2090/064* (2016.02); *A61B 2560/0214* (2013.01); *A61B 2562/028* (2013.01); *A61F 2005/563* (2013.01)

(58) Field of Classification Search
CPC ....... A61B 5/4557; A61B 5/682; A61B 5/002; A61B 2560/0214; A61B 2090/064; A61B 2562/028; A61B 2562/0247; A61B 5/6803; A61B 5/0022; A61F 5/566; A61F 2005/563; G01L 1/146; H04W 4/80; G16H 40/63; G16H 50/20
See application file for complete search history.

(56) References Cited

U.S. PATENT DOCUMENTS

| | | | | |
|---|---|---|---|---|
| 2015/0305671 | A1* | 10/2015 | Yoon | ...................... A61B 5/681 600/301 |
| 2016/0242692 | A1* | 8/2016 | McAuliffe | .............. G06F 30/00 |
| 2016/0242951 | A1* | 8/2016 | Berk | ..................... A61B 5/7405 |
| 2016/0302901 | A1* | 10/2016 | Brel | ........................ G01L 1/205 |
| 2019/0192259 | A1* | 6/2019 | Kopelman | ............. A61B 5/682 |

* cited by examiner

*Primary Examiner* — Devin B Henson
*Assistant Examiner* — Justin Xu

(57) ABSTRACT

Disclosed herein are system, method and/or device embodiments for using a wireless mouthguard with pressure sensors for measuring bite compression forces generated by a bruxism patient during sleep. A system comprises a mouthguard and a microelectromechanical system (MEMS) coupled to a portion of the mouthguard covering an axial plane of a tooth. The MEMS comprises an antenna, a capacitive sensor, a microcontroller, and a power supply. The sensor generates sensor signals corresponding to a force generated by a mouthguard wearer's bite. The MEMS may then transmit data describing the wearer's bite force over a period of time to an external computing device for display and analysis.

8 Claims, 5 Drawing Sheets

COMPUTERIZED SENSOR SYSTEM AND MOUTHGUARD DEVICE

BACKGROUND

Technical Field

Embodiments generally relate to mouthguard devices, and more specifically to mouthguards using sensors and computer systems to diagnose and monitor Bruxism and other tooth-grinding medical conditions.

Background

Bruxism is a medical condition of excessive teeth grinding or jaw clenching. It is a common behavior, reports of prevalence ranging from 8-31% in the general population. Several symptoms are commonly associated with bruxism, including hypersensitive teeth, aching jaw muscles, headaches, tooth wear, and damage to dental restorations (e.g. crowns and fillings) to teeth.

There are two main types of bruxism: one occurs during sleep (sleep bruxism) and one during wakefulness (awake bruxism). Dental damage may be similar in both types, with the symptoms of sleep bruxism tending to be worse on waking and improving during the course of the day, while the symptoms of awake bruxism may not be present at all on waking, and then worsen over the day. The causes of bruxism are not completely understood, but probably involve multiple factors. Several treatments are in use, although there is little evidence of robust efficacy for any particular treatment.

Awareness of the condition and measuring of bruxism activity are key elements of a treatment plan. Tooth wear may be brought to the person's attention during routine dental examination. Several devices have been developed that aim to objectively measure bruxism activity, either in terms of muscular activity or bite forces. However, existing devices have several drawbacks, and have been criticized for introducing a possible change in the bruxing habit and are therefore poorly representative to the native bruxing activity. Many of these devices are cumbersome and inconvenient for a person to wear during sleeping.

SUMMARY

Disclosed herein are system, method and/or device embodiments for using a wireless mouthguard with pressure sensors for measuring bite compression forces generated by a bruxism patient during sleep. A system comprises a mouthguard and a microelectromechanical system (MEMS) coupled to a portion of the mouthguard covering an axial plane of a tooth. The MEMS comprises an antenna, a capacitive sensor, a microcontroller, and a power supply. The sensor generates sensor signals corresponding to a force generated by a mouthguard wearer's bite. The MEMS may then transmit data describing the wearer's bite force over a period of time to an external computing device for display and analysis.

BRIEF DESCRIPTION OF THE DRAWINGS

The accompanying drawings are incorporated herein and form a part of the specification.

DETAILED DESCRIPTION

Provided herein are system, method and/or device embodiments, and/or combinations and sub-combinations thereof, for using a wireless mouthguard with pressure sensors for measuring bite compression forces generated by a bruxism patient during sleep.

Figure 1:
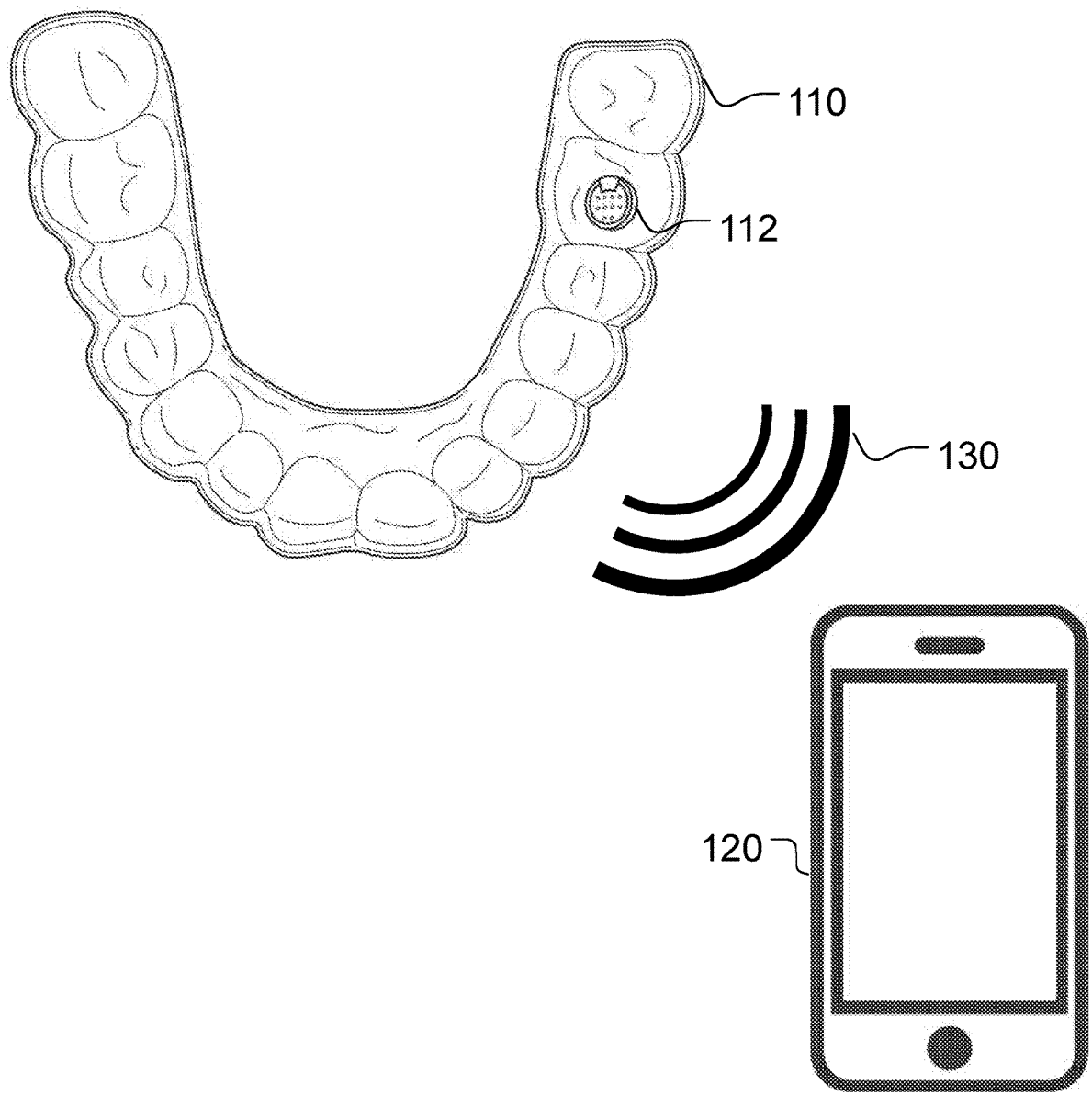
FIG. 1 illustrates a bruxism monitoring environment, according to an example embodiment. FIG.

FIG. 1 illustrates a bruxism monitoring environment 100, according to an example embodiment. A mouthguard device 110 connects to a computing device 120 through a wireless communications channel 130. The communications channel 130 may be any communications means, protocol, network or any combination thereof that is suitable for wirelessly transmitting data between computing devices, such as, by way of example, Bluetooth®, WiFi™, etc.

The body of mouthguard 110 may be shaped as an ordinary plastic mouthguard for protecting teeth such as, by way of example, a ready-made unfitted mouthguard, a mouth-adapted mouthguard adapted by heating and placing in mouth, a custom-made mouthguard made from a dental impression, etc.

Mouthguard 110 further includes a microelectromechanical system (MEMS) 112 for measuring, storing and transmitting bite force data of the patient. In particular embodiments, the mouthguard is custom-made with MEMS 112 is placed at a location identified by a dental specialist, as will be explained below. MEMS 112 may have one or more sensors that can measure a mouthguard wearer's bite force and transmit measurement data to computing device 120 for analysis and diagnosis.

A user of mouthguard 110 places the mouthguard in his/her mouth when the user desires to measure biting behavior for a period of time. For example, the user may place the mouthguard when going to bed in order to measure bruxism behavior throughout the night. In particular embodiments, a user may operate computing device 120 to configure and process the data collection process from the MEMS 112.

Figure 2:
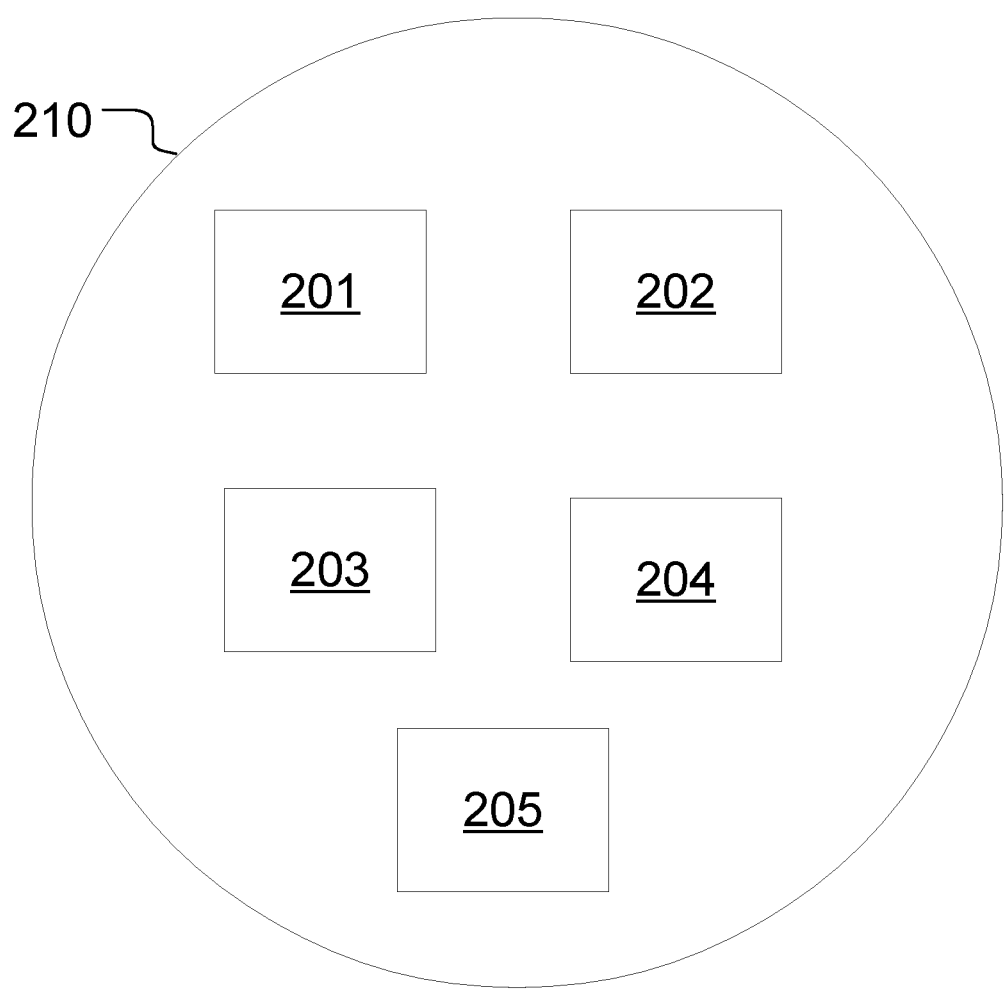
FIG. 2 shows architectural details of a MEMS, according to particular embodiments.

FIG. 2 shows architectural details of MEMS 112, according to particular embodiments. MEMS 112 includes a capacitive sensor 201, a microelectronic device 202, a transmitting antenna 203, and power supply 204. Components 201-204 are miniaturized mechanical and/or electromechanical elements that are made and integrated together using techniques of microfabrication. Components 201-204 may be integrated into an encapsulation 210 that is millimeters in size. In particular embodiments, MEMS 112 is less than 5 mm in its largest dimension, including the encapsulation. Encapsulation 210 may be made of any material suitable to resist compression forces and safe for placing in a wearer's mouth, such as suitable polyvinyl chloride (PVC) plastics.

Capacitive sensor 201 is microfabricated capacitor with mechanical system capable of adjusting a voltage passing through it depending on the distance between two plates of the capacitor. Capacitive sensor 201 can thus be used to measure a force pressing the two plates together. The MEMS may be aligned so that the sensing angle is orthogonal to a portion of the mouthguard covering an axial plane of a tooth. When thus positioned, capacitive sensor 201 may be used to measure a force biting down on MEMS 112. In particular embodiments, capacitive sensor 201 is capable of measuring forces of 1000N or 250 pounds-force.

Microelectronic device 202 may monitor one or more signals (e.g., a voltage readings) from capacitive sensor 201 and convert the signals into digital data through an analog-to-digital (AD) conversion. Microelectronic device 112 then transmits the digital data to computing device 120 through the use of transmitting antenna 203. Transmitting antenna 203 may be any antenna suitable for communicating through communications channel 130.

In particular embodiments, microelectronic device 112 comprises a microcontroller with an embedded AD converter. In particular embodiments, microelectronic device 202 comprises a special-purpose circuit for performing AD conversion and controlling the transmission antenna 203. Sensor 201 and microelectronic device 202 may be integrated to a chip made by complementary metal-oxide semiconductor (CMOS) technology.

Power supply 204 provides energy to power the operation of MEMS 112. In particular embodiments, power supply 204 can be active, i.e. having a battery—for example a Li-ion or LiMn rechargeable micro-battery. Power supply 204 may include an induction coil for charging the battery through an inductive coupling with another induction coil (e.g., coil 320 shown in FIG. 3), such as from a wireless charging station. In particular embodiments, antenna 203 includes an induction coil that can be inductively coupled to charge the battery, and thus power supply 204 does not need a separate induction coil for charging.

Figure 3:
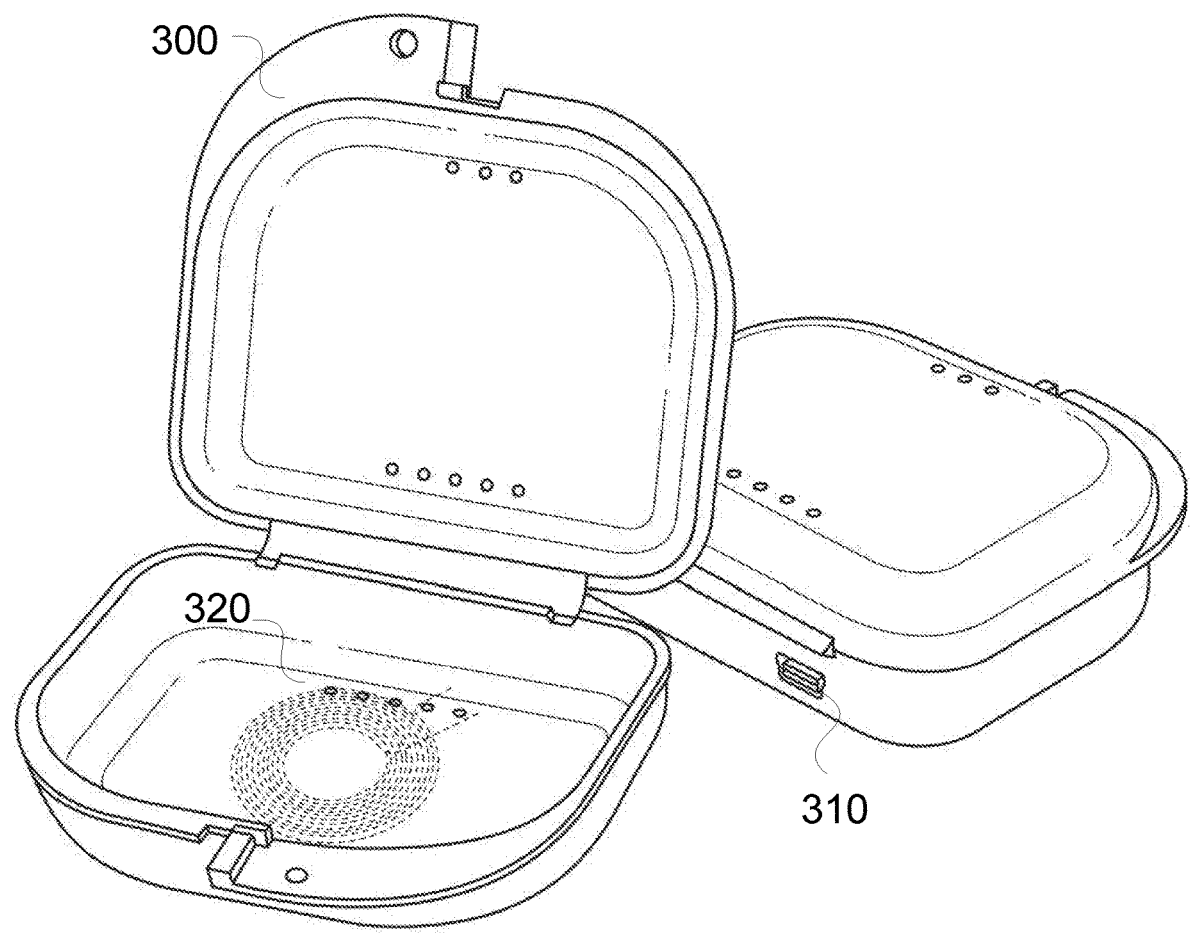
FIG. 3 shows a mouthguard storage case and charging station, according to an example embodiment.

FIG. 3 shows a mouthguard storage case and charging station 300, according to an example embodiment. A mouthguard case may include an induction coil 320 powered through an electrical connector 310 (e.g., micro-USB port, AC plug, etc.). A current passing through induction coil 320 generates an electromagnetic field. This electromagnetic field in turn generates a current through a power supply 204 induction coil, the current usable to charge a battery. In particular embodiments, power supply 204 battery permits up to 8 hours of continuous operation of MEMS 112 to measure and transmit bite force data.

In particular embodiments, power supply 204 is passive, i.e. having no battery, in which case MEMS 112 is intermittently activated when antenna 203 or a separate induction coil receives an external charge, e.g., from computing device 120.

In particular embodiments, MEMS 112 further includes a storage component 205 for storing data collected from sensor 201. In particular embodiments, MEMS 112 gathers data for a period of time (e.g., a night) and stores the data in storage component 205. Data storage component 205 may be any storage technology suitable for inclusion in a MEMS device such as, by way of example, volatile memory (RAM), solid-state non-volatile memory (flash memory), etc. While data storage 205 is described as a separate component, it should be understood that data storage 205 may form part of another component, such as microelectronic device 202.

In particular embodiments, MEMS 112 transmits the data in real-time or at periodic intervals to computing device 120. In particular embodiments, MEMS 112 stores the data and then transmits it at a later time based to computing device 120, for example, in response to instructions received from computing device 120. As such, MEMS 112 may transmit data as it gathers sensor readings, or may aggregate multiple sensor readings and transmit them at a later time. As an example, MEMS 112 may measure pressure every minute for 8 hours, and may then transmit all 480 measurements at the end of the 8-hour period.

Figure 4:
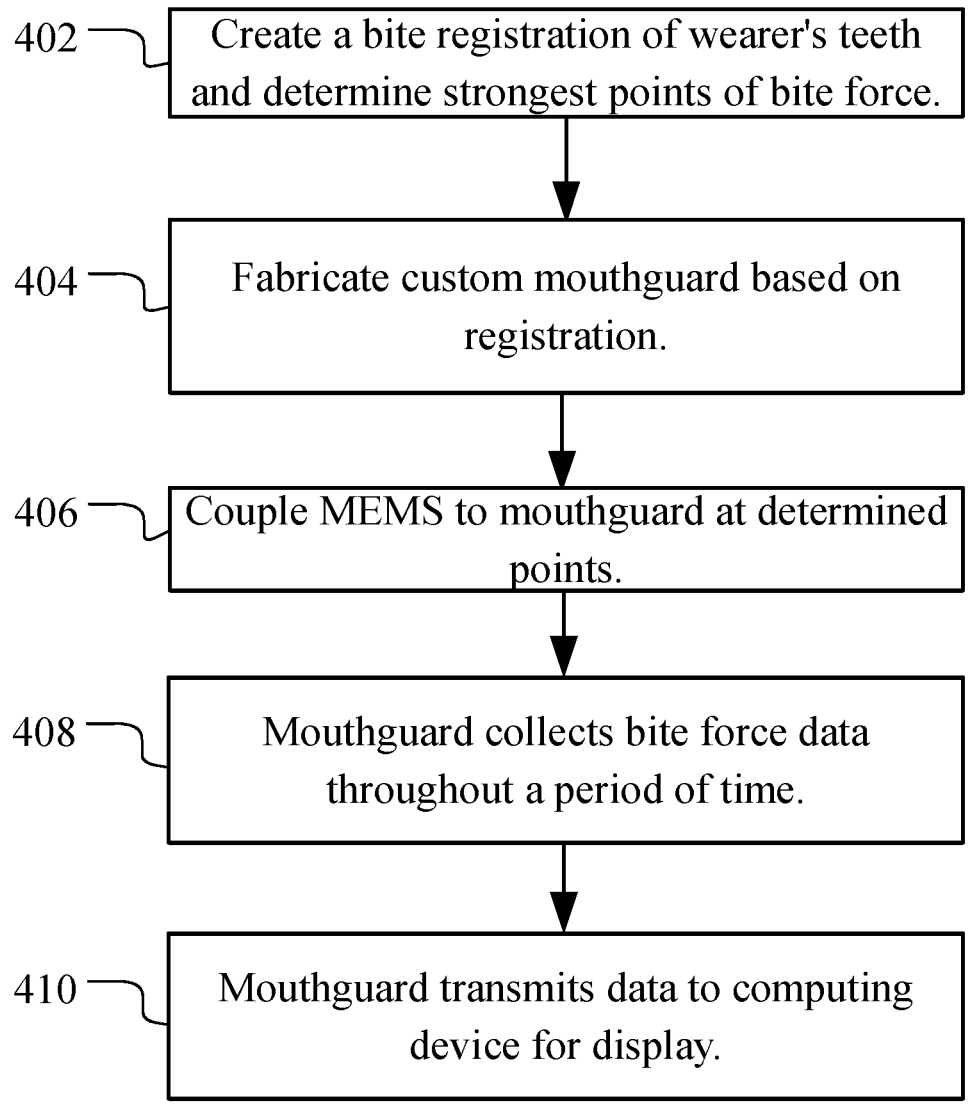
FIG. 4 is a flowchart of a method for fabricating and using a wireless mouthguard with pressure sensors for measuring bite compression forces, according to an example embodiment.

FIG. 4 is a flowchart of a method 400 for fabricating and using a wireless mouthguard with pressure sensors for measuring bite compression forces, according to an example embodiment. At step 402, a bite registration of the teeth is examined to determine the strongest points of bite force in a patient's mouth. At step 404, a custom mouthguard is fabricated based on a bite registration of the wearer. At step 406, one or more MEMS 112 are coupled to the mouthguard at the marked points. In particular embodiments, steps 404 and 406 may be done together if, for example, the sensor is embedded within the mouthguard material. In this manner, the mouthguard system will measure the wearer's strongest points of bite force. At step 408, a wearer wears the mouthguard for a period of time (e.g., at night time). At step 410, sensor data is transmitted to a computing device 120 for analysis and diagnosis. Computing device 120 may be configured to display information in any suitable format through a graphical user interface.

The embodiments disclosed above are only examples, and the scope of this disclosure is not limited to them. Particular embodiments may include all, some, or none of the components, elements, features, functions, operations, or steps of the embodiments disclosed above. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

Figure 5:
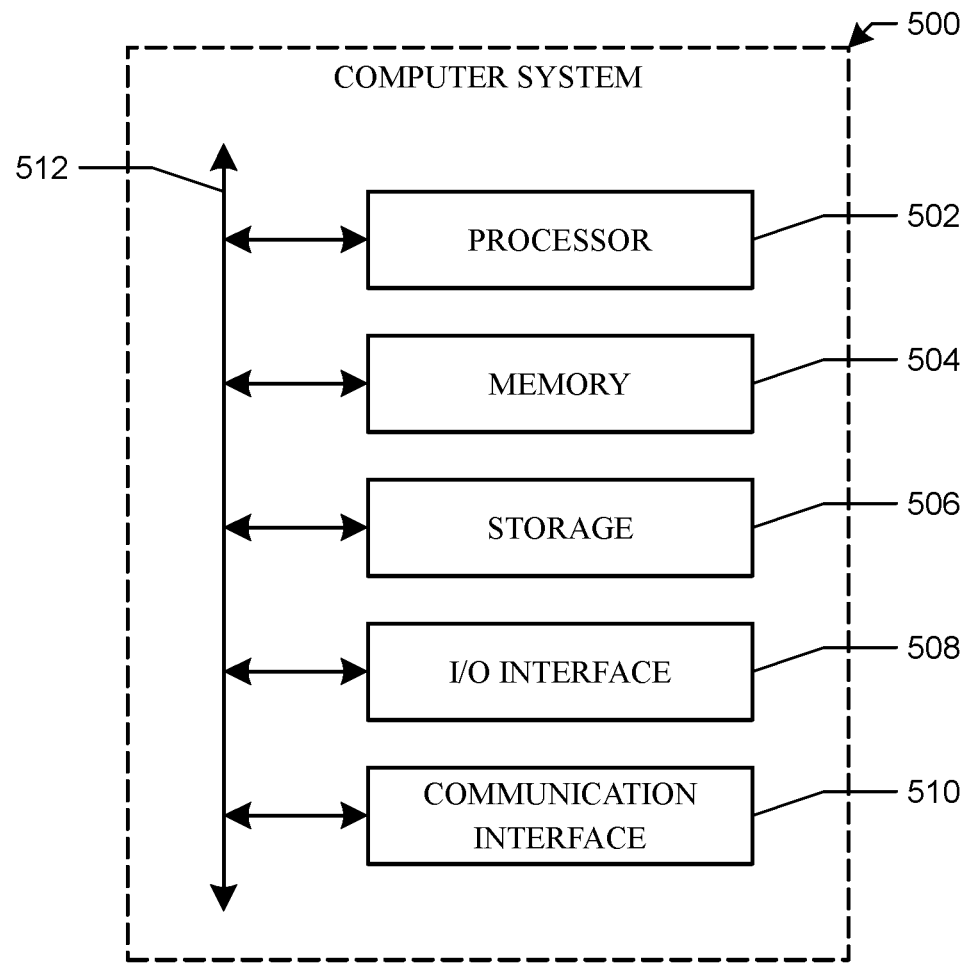
FIG. 5 is an example computer system useful for implementing various embodiments.

FIG. 5 illustrates an example computer system 500. In particular embodiments, one or more computer systems 500 perform one or more steps of one or more methods described or illustrated herein. In particular embodiments, one or more computer systems 500 provide functionality described or illustrated herein, such as those of computing device 120. In particular embodiments, software running on one or more computer systems 500 performs one or more steps of one or more methods described or illustrated herein or provides functionality described or illustrated herein. Particular embodiments include one or more portions of one or more computer systems 500. Herein, reference to a computer system may encompass a computing device, and vice versa, where appropriate. Moreover, reference to a computer system may encompass one or more computer systems, where appropriate.

This disclosure contemplates any suitable number of computer systems 500. This disclosure contemplates computer system 500 taking any suitable physical form. As example, computer system 500 may be an embedded computer system, a desktop computer system, a laptop or notebook computer system, a mainframe, a mobile telephone, a personal digital assistant (PDA), a server, a tablet computer system, or a combination of two or more of these. Where appropriate, computer system 500 may include one or more computer systems 500; be unitary or distributed; span multiple locations; span multiple machines; span multiple data centers; or reside in a cloud, which may include one or more cloud components in one or more networks. Where appropriate, one or more computer systems 500 may perform without substantial spatial or temporal limitation one or more steps of one or more methods described or illustrated herein. As an example, one or more computer systems 500 may perform in real time or in batch mode one or more steps of one or more methods described or illustrated herein. One or more computer systems 500 may perform at different times or at different locations one or more steps of one or more methods described or illustrated herein, where appropriate.

In particular embodiments, computer system 500 includes a processor 502, memory 504, storage 506, an input/output (I/O) interface 508, a communication interface 510, and a bus 512. Although this disclosure describes and illustrates a particular computer system having a particular number of particular components in a particular arrangement, this disclosure contemplates any suitable computer system having any suitable number of any suitable components in any suitable arrangement.

In particular embodiments, processor 502 includes hardware for executing instructions, such as those making up a computer program. As an example, to execute instructions, processor 502 may retrieve (or fetch) the instructions from an internal register, an internal cache, memory 504, or storage 506; decode and execute them; and then write one or more results to an internal register, an internal cache, memory 504, or storage 506. In particular embodiments, processor 502 may include one or more internal caches for data, instructions, or addresses. This disclosure contemplates processor 502 including any suitable number of any suitable internal caches, where appropriate. In particular embodiments, processor 502 may include one or more internal registers for data, instructions, or addresses. This disclosure contemplates processor 502 including any suitable number of any suitable internal registers, where appropriate. Where appropriate, processor 502 may include one or more arithmetic logic units (ALUs); be a multi-core processor; or include one or more processors 502. Although this disclosure describes and illustrates a particular processor, this disclosure contemplates any suitable processor.

In particular embodiments, memory 504 includes main memory for storing instructions for processor 502 to execute or data for processor 502 to operate on. As an example, computer system 500 may load instructions from storage 506 or another source (such as, for example, another computer system 500) to memory 504. Processor 502 may then load the instructions from memory 504 to an internal register or internal cache. To execute the instructions, processor 502 may retrieve the instructions from the internal register or internal cache and decode them. During or after execution of the instructions, processor 502 may write one or more results (which may be intermediate or final results) to the internal register or internal cache. Processor 502 may then write one or more of those results to memory 504. In particular embodiments, processor 502 executes only instructions in one or more internal registers or internal caches or in memory 504 (as opposed to storage 506 or elsewhere) and operates only on data in one or more internal registers or internal caches or in memory 504 (as opposed to storage 506 or elsewhere). One or more memory buses (which may each include an address bus and a data bus) may couple processor 502 to memory 504. Bus 512 may include one or more memory buses, as described below. In particular embodiments, memory 504 includes random access memory (RAM). This RAM may be volatile memory, where appropriate Memory 504 may include one or more memories 504, where appropriate. Although this disclosure describes and illustrates particular memory, this disclosure contemplates any suitable memory.

In particular embodiments, storage 506 includes mass storage for data or instructions. As an example, storage 506 may include a hard disk drive (HDD), a floppy disk drive, flash memory, an optical disc, a magneto-optical disc, magnetic tape, or a Universal Serial Bus (USB) drive or a combination of two or more of these. Storage 506 may include removable or non-removable (or fixed) media, where appropriate. Storage 506 may be internal or external to computer system 500, where appropriate. In particular embodiments, storage 506 is non-volatile, solid-state memory. In particular embodiments, storage 506 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 506 taking any suitable physical form. Storage 506 may include one or more storage control units facilitating communication between processor 502 and storage 506, where appropriate. Where appropriate, storage 506 may include one or more storages 506. Although this disclosure describes and illustrates particular storage, this disclosure contemplates any suitable storage.

In particular embodiments, I/O interface 508 includes hardware, software, or both, providing one or more interfaces for communication between computer system 500 and one or more I/O devices. Computer system 500 may include one or more of these I/O devices, where appropriate. One or more of these I/O devices may enable communication between a person and computer system 500. As an example, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 508 for them. Where appropriate, I/O interface 508 may include one or more device or software drivers enabling processor 502 to drive one or more of these I/O devices. I/O interface 508 may include one or more I/O interfaces 508, where appropriate. Although this disclosure describes and illustrates a particular I/O interface, this disclosure contemplates any suitable I/O interface.

In particular embodiments, communication interface 510 includes hardware, software, or both providing one or more interfaces for communication (such as, for example, packet-based communication) between computer system 500 and one or more other computer systems 500 or one or more networks. As an example, communication interface 510 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 510 for it. As an example, computer system 500 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 500 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 500 may include any suitable communication interface 510 for any of these networks, where appropriate. Communication interface 510 may include one or more communication interfaces 510, where appropriate. Although this disclosure describes and illustrates a particular communication interface, this disclosure contemplates any suitable communication interface.

In particular embodiments, bus 512 includes hardware, software, or both coupling components of computer system 500 to each other. As an example, bus 512 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 512 may include one or more buses 512, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A system comprising: a microelectromechanical system (MEMS) coupled to a portion of a mouthguard covering an axial plane of a tooth, wherein the MEMS comprises:
   an antenna,
   exactly one capacitive sensor configured to generate sensor signals corresponding to a force generated by a mouthguard wearer's bite,
   a microcontroller communicatively coupled to the exactly one capacitive sensor, the microcontroller comprising at least one processor and a memory and configured to receive the sensor signals from the exactly one capacitive sensor and transmit communication signals that cause the antenna to transmit data representing the sensor signals, wherein the data describes the wearer's bite force over a period of time;
   a power supply connected to the exactly one capacitive sensor, microcontroller, and antenna, wherein the exactly one or more capacitive sensor is embedded in the mouthguard at a strongest point of bite force determined by examining a bite registration of the teeth; and
   wherein the MEMS is less than 5 mm in its maximum dimension.

2. The system of claim 1, wherein the antenna transmits the data to an external computing device.

3. The system of claim 2, wherein the antenna transmits the data over a Bluetooth channel to the external computing device.

4. The system of claim 1, wherein the power supply comprises a rechargeable battery.

5. The system of claim 4, wherein the MEMS further comprises a first induction coil configured to receive wireless power from an electromagnetic field to charge the rechargeable battery.

6. The system of claim 5, further comprising a storage case for the system, the storage case comprising a wireless charging station for the MEMS rechargeable battery, the charging station comprising a second induction coil for creating an alternating electromagnetic field that charges the MEMS rechargeable battery.

7. A method for diagnosing a tooth-grinding condition, comprising:
- determining one or more strongest points of bite force in a person's bite by examining a bite registration of the person's teeth;
- fabricating a mouthguard according to the bite registration;
- embedding exactly one capacitive sensor, wherein the sensor is less than 5 mm in its maximum dimension, in the mouthguard at one of the determined one or more strongest points of bite force.

8. The method of claim 7, further comprising:
preparing a microelectromechanical system (MEMS); and
coupling the MEMS to a portion of the mouthguard covering an axial plane of a tooth, the MEMS comprising:
- an antenna,
- the exactly one capacitive sensor,
- the microcontroller, wherein the microcontroller:
  - is communicatively coupled to the exactly one capacitive sensor, comprises at least one processor and a memory,
  - is configured to receive sensor signals from the exactly one capacitive sensor, and
  - is configured to transmit the data via the antenna, and
- a power supply connected to the exactly one capacitive sensor, the microcontroller, and the antenna.

\* \* \* \* \*